United States Patent
Mercer et al.

(10) Patent No.: US 9,314,576 B2
(45) Date of Patent: Apr. 19, 2016

(54) MEDICATED MODULE WITH AUTOMATIC RESERVOIR ENGAGEMENT

(75) Inventors: David Richard Mercer, Warwickshire (GB); Thomas Urs Thueer, Oxfordshire (GB); Garen Kouyoumjian, Warwichshire (GB); Malcolm Stanley Boyd, Warwickshire (GB)

(73) Assignee: SANOFI-AVENTIS DEUTSCHLAND GMBH, Frankfurt am Main (DE)

(*) Notice: Subject to any disclaimer, the term of this patent is extended or adjusted under 35 U.S.C. 154(b) by 184 days.

(21) Appl. No.: 13/989,021

(22) PCT Filed: Nov. 28, 2011

(86) PCT No.: PCT/EP2011/071139
§ 371 (c)(1),
(2), (4) Date: May 22, 2013

(87) PCT Pub. No.: WO2012/072562
PCT Pub. Date: Jun. 7, 2012

(65) Prior Publication Data
US 2013/0245563 A1    Sep. 19, 2013

(30) Foreign Application Priority Data
Nov. 29, 2010  (EP) .................................... 10192995

(51) Int. Cl.
*A61M 5/32* (2006.01)
*A61M 5/14* (2006.01)
(Continued)

(52) U.S. Cl.
CPC ........... *A61M 5/3294* (2013.01); *A61M 5/1409* (2013.01); *A61M 5/1413* (2013.01);
(Continued)

(58) Field of Classification Search
CPC ............. A61M 2005/1402; A61M 2005/3247; A61M 2005/3267; A61M 2205/581; A61M 2205/584; A61M 2206/10; A61M 5/1409; A61M 5/1413; A61M 5/2066; A61M 5/2448; A61M 5/2466; A61M 5/3146; A61M 5/3293; A61M 5/3294; A61M 5/347; A61M 2005/247; A61M 2005/2474; A61J 1/2013; A61J 1/14
USPC ............. 604/82–92, 206, 234, 241, 131–141, 604/181–185, 187–188, 191, 192, 197, 198
See application file for complete search history.

(56) References Cited

U.S. PATENT DOCUMENTS 5,330,426 A     7/1994  Kriesel et al.
6,209,738 B1 *  4/2001  Jansen et al. .................. 215/247
(Continued)

FOREIGN PATENT DOCUMENTS

EP     0288443 A1     10/1988
WO     8802265 A1      4/1988
WO     2004108205 A1  12/2004

OTHER PUBLICATIONS

International Preliminary Report on Patentability mailed Jun. 13, 2013 in International Application No. PCT/EP2011/071139.
(Continued)

*Primary Examiner* — Nathan R Price
*Assistant Examiner* — Weng Lee
(74) *Attorney, Agent, or Firm* — McDonnell Boehnen Hulbert & Berghoff LLP (57) ABSTRACT

A medicated module for an injection system to co-deliver at least two medicaments is disclosed where a primary delivery device containing a primary medicament accepts a medicated module containing a single dose of a secondary medicament and where both medicaments are delivered through a hollow needle. The medicated module does not require the user to manually engage a reservoir containing the secondary medicament. Instead, a rotating housing automatically activates the reservoir when the needle guard is retracted. The needle guard prevents accidental needle sticks after an injection, and locks after dose delivery.

18 Claims, 6 Drawing Sheets

(51) Int. Cl.
    *A61M 5/20*    (2006.01)
    *A61M 5/24*    (2006.01)
    *A61M 5/31*    (2006.01)
    *A61M 5/34*    (2006.01)

(52) U.S. Cl.
    CPC ............ *A61M5/2066* (2013.01); *A61M 5/2448* (2013.01); *A61M 5/2466* (2013.01); *A61M 5/3146* (2013.01); *A61M 5/3293* (2013.01); *A61M 5/347* (2013.01); *A61M 2005/1402* (2013.01); *A61M 2005/3247* (2013.01); *A61M 2005/3267* (2013.01); *A61M 2205/581* (2013.01); *A61M 2205/584* (2013.01); *A61M 2206/10* (2013.01)

(56) References Cited

U.S. PATENT DOCUMENTS

| | | | |
|---|---|---|---|
| 6,562,002 | B1 | 5/2003 | Taylor |
| 7,597,685 | B2 | 10/2009 | Olson |
| 2008/0281271 | A1 | 11/2008 | Griffiths et al. |

OTHER PUBLICATIONS

Machine Translation of WO 88/02265.

English Translation of the Notice of Reasons for Rejection issued in Japanese Patent Application No. 2013-540404 dated Sep. 8, 2015.

\* cited by examiner

MEDICATED MODULE WITH AUTOMATIC RESERVOIR ENGAGEMENT

CROSS REFERENCE TO RELATED APPLICATIONS

The present application is a U.S. National Phase application pursuant to 35 U.S.C. §371 of International Application No. PCT/EP2011/071139 filed Nov. 28, 2011, which claims priority to European Patent Application No. 10192995.8 filed Nov. 29, 2010. The entire disclosure contents of these applications are herewith incorporated by reference into the present application.

FIELD OF INVENTION

This invention relates to medical devices and methods of delivering at least two drug agents from separate reservoirs using devices having only a single dose setting mechanism and a single dispense interface. A single delivery procedure initiated by the user may cause a non-user settable dose of a second drug agent or secondary medicament and a variable set dose of a first drug agent or primary medicament to be delivered to the patient. The drug agents may be available in two or more reservoirs, containers or packages, each containing independent (single drug compound) or pre-mixed (co-formulated multiple drug compounds) drug agents. Specifically, the present disclosure concerns a medicated module where the user does not have to manually select or set the module to dispense the second drug agent. Activation of the needle guard may automatically cause the reservoir of secondary medicament to engage with dispensing conduits to allow a set dose of the primary medicament and a single fixed dose of the of the secondary medicament to be injected. The present disclosure is of particular benefit where the therapeutic response can be optimized for a specific target patient group, through control and definition of the therapeutic profile.

BACKGROUND

For example, in some cases it might be beneficial to treat a diabetic with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems when delivering two medicaments or active agents simultaneously. The two active agents may interact with each other during the long-term, shelf life storage of the formulation. Therefore, it is advantageous to store the active components separately and only combine them at the point of delivery, e.g. injection, needle-less injection, pumps, or inhalation. However, the process for combining the two agents needs to be simple and convenient for the user to perform reliably, repeatedly and safely.

A further problem is that the quantities and/or proportions of each active agent making up the combination therapy may need to be varied for each user or at different stages of their therapy. For example one or more actives may require a titration period to gradually introduce a patient up to a "maintenance" dose. A further example would be if one active requires a non-adjustable fixed dose while the other is varied in response to a patient's symptoms or physical condition. This problem means that pre-mixed formulations of multiple active agents may not be suitable as these pre-mixed formulations would have a fixed ratio of the active components, which could not be varied by the healthcare professional or user.

Additional problems may arise where a multi-drug compound therapy is required, because many users cannot cope with having to use more than one drug delivery system or make the necessary accurate calculation of the required dose combination. This is especially true for users with dexterity or computational difficulties. In some circumstances it may also be necessary to perform a priming procedure of the device and/or needle cannulae before dispensing the medicaments. Likewise, in some situations, it may be necessary to bypass one drug compound and to dispense only a single medicament from a separate reservoir.

SUMMARY

Accordingly, there exists a strong need to provide devices and methods for the delivery of two or more medicaments in a single injection or delivery step that is simple for the user to perform. The present disclosure may overcome the above-mentioned problems by providing separate storage containers for two or more active drug agents that are then only combined and/or delivered to the patient during a single delivery procedure. Setting a dose of one medicament automatically fixes or determines the dose of the second medicament (i.e. non-user settable). The present disclosure may also give the opportunity for varying the quantity of one or both medicaments. For example, one fluid quantity can be varied by changing the properties of the injection device (e.g. dialing a user variable dose or changing the device's "fixed" dose). The second fluid quantity can be changed by manufacturing a variety of secondary drug containing packages with each variant containing a different volume and/or concentration of the second active agent. The user or healthcare professional would then select the most appropriate secondary package or series or combination of series of different packages for a particular treatment regime.

The present disclosure also provides a medicated module that automatically causes the reservoir of secondary medicament to come into fluid communication with the primary medicament upon activation of the needle guard. This eliminates the need for the user to manually set or adjust the medicated module after performing a priming step.

These and other advantages will become evident from the following more detailed description of the invention.

The present disclosure allows complex combinations of multiple drug compounds within a single drug delivery system. The disclosure allows the user to set and dispense a multi-drug compound though one single dose setting mechanism and a single dispense interface. This single dose setter may control the mechanism of the device such that a pre-defined combination of the individual drug compound is delivered when a single dose of one of the medicaments is set and dispensed through the single dispense interface.

By defining the therapeutic relationship between the individual drug compounds the disclosed delivery device may help to ensure that a patient/user receives the optimum therapeutic combination dose from a multi-drug compound device without the inherent risks associated with multiple inputs where the user has to calculate and set the correct dose combination every time he uses the device. The medicaments can be fluids, defined herein as liquids or powders that are capable of flowing and that change shape at a steady rate when acted upon by a force tending to change its shape. Alternatively, one of the medicaments may be a solid that is carried, solubilized or otherwise dispensed with another fluid medicament.

According to one specific aspect, the present disclosure is of particular benefit to users with dexterity or computational difficulties as the single input and associated predefined therapeutic profile may remove the need for them to calculate their prescribed dose every time they use the device and the single input allows considerably easier setting and dispensing of the combined compounds.

In a preferred embodiment a master or primary drug compound, such as insulin, contained within a multiple dose, user selectable device could be used with a single use, user replaceable, module that contains a single dose of a secondary medicament and the single dispense interface. When connected to the primary device the secondary compound may be activated/delivered on dispense of the primary compound. Although the present disclosure specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with the drug delivery system and the medicated module of the present disclosure.

For the purposes of our invention the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys (B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des (B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH2).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

The present disclosure is directed to alternative mechanisms for automatically engaging a reservoir in a medicated module to place the reservoir in fluid communication with needle cannula and preferably with a primary medicament from a primary drug delivery device. The mechanisms of the present disclosure use the needle guard movement to drive rotating housings in the medicated module to cause the reservoir to engage needle cannula. By combining the rotating housings with helical threads, ramps or slots, axial movement of either the reservoir or cannulae hubs, at a different rate to the needle guard, can be achieved. By adjusting the geometry of the helical features the relative movement of each element and the overall actuation force profile can be varied. The mechanisms of the present disclosure provides for relative movement of the cannula hubs and the reservoir with regards to each other.

In one embodiment there is provided a medicated module attachable to a drug delivery device that comprises an outer housing having an inner surface, a proximal end and a distal end, where the proximal end has a connector configured for attachment to a drug delivery device. A bypass housing is located inside the outer housing that is configured to contain a reservoir preferably having a single dose of a medicament. The module further has two needle hubs positioned above and below the reservoir, each containing a double-ended needle cannula. There is also a rotating housing located within the outer housing that in some embodiments is the same structure as the bypass housing. The rotating housing has an internal surface and an external surface, where the external surface is engaged with the inner wall of the needle guard such that axial movement of the needle guard in the proximal direction causes rotation of the rotating housing relative to the outer housing and also causes the lower needle to engage with the reservoir to establish fluid communication with the medicament.

The medicated module assembly of the present disclosure contains a needle guard that can reduce the risk of accidental needle sticks before and after use, reduce the anxiety of users suffering from needle phobia as well as preventing a user from using the device a subsequent time when the additional medicament has already been expelled. The needle guard has a inner wall and an outer wall, where the outer wall is splined to the outer housing to prevent rotation of the needle guard when it is moved axially.

The needle guard is preferably configured with a solid planar surface at its distal end that provides a large surface area that reduces the pressure exerted on the patient's skin, which allows the user to experience an apparent reduction in the force exerted against the skin. Preferably, the planar surface covers the entire distal end of the needle guard with the exception of a small needle pass through hole aligned axially with the needle. Preferably, the pass through hole size should be large enough for the user to see that the device is primed (i.e., a drop or more of medicament) while not being so large that it is still possible to reach the end of the needle with a finger (i.e. needle stick injuries before or after use). This difference between the hole size and cannula diameter is to allow for tolerances, to allow users to see the drop of liquid on the end of the cannula after priming (whether a transparent or non-transparent needle guard is used) while keeping the size small enough to prevent accidental needle stick injuries.

Further, the needle guard or shield is configured to move axially in both the distal and proximal directions when pressed against and removed from an injection site. When the needle assembly is removed or withdrawn from the patient, the needle guard is returned to post-use extended position. A locking mechanism on the needle guard, outer housing, rotating housing, or combination of these can be used to securely lock the needle guard from further substantial axial movement at the completion of the injection to further lock the medicated module from any further use. Alternatively or additionally, the locking mechanism may also prevent the needle(s) and/or bypass component from being able to substantially move within the system even if the needle guard is held in an axially locked condition. By "substantial" movement we do not mean the typical amount of "play" in a system, but instead we mean that the needle guard and/or distal needle do not move axially a distance that exposes the distal end of the cannula once it is locked out.

One goal of the present disclosure is to eliminate the need to have the user manually operate the medicated module to change the state of the module from a priming state to a combination dose delivery state. Manually operated devices are sometimes not as intuitive as they could be and raise the risk of accidental misuse. The present disclosure may solve this problem by utilizing a rotating housing that is moved by the retraction of needle guard thus activating the state change from prime dose to combination dose. The mechanism aims to make this actuation imperceptible to the user, consequently making the user experience of the module very similar to that of a standard commercially available and accepted needle or safety needle (i.e. unpack module, attach to a drug delivery device, prime drug delivery device, inject a set dose along with single dose in the module). In this way, the module mechanism aims to reduce the risk of unintentional misuse and to improve usability by replicating an already accepted practice for similar injection methods.

As the module mechanism does not require the user to access external features on the module for the purposes of actuation, the number of components and subsequent module size can be reduced/optimized. These factors make the mechanism ideal for a single-use, high-volume manufacture, and disposable device application. Alternatively, as the actuation is driven by a single action, the system lends itself to a resettable actuation mechanism. The preferred embodiment described below is the single use (non-resettable) version. In certain embodiments the rotating housing causes the lower hub to move axially, and in certain embodiments to rotate as well, as the needle guard is retracted. The needle guard is restrained rotationally with regard to the outer housing, but is free to move axially, between defined constraints, within the outer housing.

The user pressing the distal face of the needle guard against the skin causes axial motion of the needle guard in the proximal direction. This axial motion of the needle guard causes a rotation of a housing through the engagement and action of an inward-facing drive tooth on the needle guard, or by threaded engagement, or by providing a track on the inner wall of the needle guard. After sufficient axial travel of the needle guard, the rotation of the housing will have caused the reservoir to come into fluid engagement with the upper and lower needle cannula after piercing the reservoir seals, moving it from a state of priming to combination dose delivery.

Further axial and proximal movement of the needle guard is required in order to pierce the skin, which compresses the biasing member against the outer housing therefore creating a force that allows the needle guard to extend to it's locked position after removal from the patient's skin or injection site. In normal use, once the drug has been dispensed and the needle is removed from the skin, the needle guard is allowed to return axially in the distal direction under the relaxation of the biasing member as it releases its stored energy. At some point along its return travel, a lock out mechanism is triggered locking out the needle guard from further use or exposing the needle. Should the user remove the device from the skin without dispensing fluid, but after the "commit" point has been passed, the needle guard would return to an extended position and lock out as previously described.

In one embodiment a medicated module may be attachable to a drug delivery device. The medicated module may comprise an outer housing having an inner surface, an upper proximal end and a lower distal end, where the proximal end has an upper hub having a connector configured for attachment to a drug delivery device. A bypass housing may be arranged within the outer housing. The bypass housing may comprise a reservoir containing a single dose of a medicament. The reservoir may be arranged within the bypass housing. A lower hub may be arranged below the reservoir holding a lower needle. An upper needle hub may be arranged above the reservoir holding an upper needle. A needle guard configured to prevent accidental needle stick may be slidably connected to the inner surface of the outer housing to prevent rotation of the needle guard when moved axially. The needle guard may have an inner wall. Further the external surface of a rotating housing may be engaged with the inner wall of the needle guard. This engagement may enable at least rotary movement of the rotating housing such that axially movement of the needle guard in the proximal direction causes rotation of the rotating housing. The rotating housing may have an internal surface. The needle guard may be engaged with at least one of the rotating housing and the lower needle hub. The rotating housing may be engaged with at least one of the bypass housing and at least one needle hub. Axially movement of the needle guard (42) in the proximal direction and rotation of the rotating housing (53) may cause engagement of the lower needle with the reservoir to establish fluid communication with the medicament.

According to one embodiment there is provided a medicated module assembly as described herein attachable to a drug delivery device, preferably a pen shaped injection device, where the medicated module assembly comprises an outer housing having a proximal end and a distal end, where the proximal end has an upper hub holding a first double-ended needle cannula and a connector configured for attachment to a drug delivery device. The hub can be a separate part from the housing or integral, for example molded as part of the housing. The connector can be any connector design, such as threads, snap fits, bayonet, luer lock, or combination of these designs.

Preferably, two needle cannula are used, a distal cannula and a proximal cannula, with both cannulae preferably being doubled-ended for piercing a septum or seal and for piercing skin. The distal needle is mounted in a lower hub and the proximal needle is mounted in the upper hub of the outer housing, each using any technique known to those skilled in the art, such as welding, gluing, friction fit, over-molding and the like. The medicated module assembly also contains a biasing member, preferably a compression spring. The biasing member is preferably in a pre-compressed state and positioned between the proximal inner face of the needle guard and the outer housing. Although a preferred biasing member is a spring, any type of member that produces a biasing force will work.

The medicated module assembly of the present disclosure automatically, once triggered, changes state from (1) a pre-use or priming state, where a small amount of primary medicament flows in a bypass around the reservoir containing a single dose of the secondary medicament, to (2) a ready-to-use or combination dose state, where both the upper and lower cannulae are in fluidic engagement with the fixed dose of the secondary medicament within the module and where a set dose of the primary medicament can be injected along with the non-settable single dose of secondary medicament in the reservoir, and finally to (3) a locked out state, where the needle guard is prevented from substantial proximal movement. The outer housing preferably has a window or indicator that shows the various states of the module. The indicator can be a pip, knob, button, or the like that protrudes through the outer surface of the proximal end of the needle guard and visually shows the user whether the module is in the pre-use or ready-to-use state. It may also be a visual indicator, e.g. showing colors or symbols, or a tactile or audible indicator. Preferably, user noticeable indicia indicate both a pre-use priming position and a locked position of the needle guard after the medicated module assembly has been used to perform an injection.

Inside the bypass housing there is a cavity that contains the reservoir or capsule, which comprises the single dose of medicament. As the needle guard is retracted during an injection, the reservoir is moved proximally inside the cavity, thus decreasing the cavity volume. This allows the seals of the capsule to be pierced at its top and bottom by the needle cannula such that the medicament can be expelled from the reservoir during dose delivery. When connected to a drug delivery device containing a primary medicament and prior to piercing the seals of the reservoir, the needle cannulae are only in fluid communication with the primary medicament and a fluid flow path that bypasses the capsule. Preferably, a channel on the inside surface of the bypass housing is part of this fluid flow path and is used in the priming function of the drug delivery device. Alternatively, the channel can be on the outside surface of the reservoir.

In another embodiment of the medicated module the inner wall of the needle guard is in threaded engagement with the external surface of the rotating housing and the internal surface of the rotating housing is in threaded engagement with the lower and upper hubs such that the rotation of the rotating housing causes the upper hub to move distally and the lower hub to move proximally whereby the upper needle and the lower needle come into fluid communication with the medicament. This is preferably accomplished using threads of opposite hand, e.g., where the threaded connection (T1) between the inner wall of the needle guard and the external surface of the rotating housing is a right handed thread, the threaded connection between internal surface of the rotating housing and the lower hub (T3) would also be a right handed thread, whereas the threaded connection between the internal surface of the rotating housing and the upper hub (T2) would need to be a left handed thread. Alternatively, the right and left handed threads can be switched. In a formula, thread types T1 and T3 are the same and T2 is the opposite, this ensures that the respective hubs move in the correct direction as the needle guard is retracted.

In yet another embodiment the inner wall of the needle guard has a drive tooth that engages a non-linear track on an outside surface of the rotating housing, where the internal surface of the rotating housing has a radial protrusion that engages the lower hub causing it to move proximally when the needle guard is retracted into the outer housing. By having the lower hub is splined to a bypass housing on an outside surface and having an inside surface that is splined to the outer housing, this prevents rotation of the lower hub and the bypass housing. In other words, an inside surface of the lower hub is splined to the bypass housing and an inside surface of the bypass housing is splined to the outer housing. This prevents rotation of the lower hub and bypass housing. A second radial protrusion on the internal surface of the rotating housing engages a track on the outside surface of the bypass housing to cause the bypass housing to move proximally when the needle guard retracts. Proximal movement of the lower hub and the bypass housing causes the lower needle and upper needle to come into fluid engagement with the medicament. When the lower hub and the bypass housing are moved proximally the lower and upper needle are caused to engage the reservoir and come into fluid engagement with the medicament.

In another embodiment of the medicated module, the inner wall of the needle guard has a non-linear track that engages a radial protrusion on an outside surface of the lower hub such that proximal axial movement of the needle guard causes the lower hub to rotate and move proximally to cause the lower needle to engage the reservoir. In this embodiment the rotating housing is the same structure as the bypass cavity and has a radial protrusion on the external surface that engages the track. An inner housing is connected to the outer housing and has a non-linear track engaged with the radial protrusions on the lower hub and on the rotating housing, where the non-linear track of the inner housing causes the lower hub and rotating housing to move axially as they are rotated. Proximal movement of the lower hub and the rotating housing may cause the lower needle and upper needle to come into fluid engagement with the medicament. When the lower hub and the rotating housing are moved proximally the lower and upper needle are caused to engage the reservoir and come into fluid engagement with the medicament.

The mechanisms of the present disclosure provide for relative movement of the lower hub, the reservoir, the bypass housing, and the upper hub with regards to each other. Relative movement of the lower hub and the bypass housing (or reservoir) towards each other could cause engagement of the lower needle with the reservoir to establish fluid communication with the medicament. Relative movement of the upper hub and the bypass housing (or reservoir) towards each other could cause engagement of the upper needle with the reservoir to establish fluid communication with the medicament.

A further aspect of the invention relates to a method of dispensing a fixed dose of one medicament and a variable dose of a primary medicament from separate reservoirs that involves the steps of first attaching a medicated module to a delivery device set in a pre-use or prime only state. The user can prime the dose delivery device using only the primary medicament and bypassing the secondary medicament. After priming the user begins the injection and the needle guard begins to retract and the module automatically changes to second state that allows a combination delivery of the two medicaments. Upon completion of the delivery procedure and refraction of the needle from the injection site, the extension of the needle guard automatically changes the module to a third state.

During dispense, substantially the entire amount of secondary medicament has been expelled as well as the selected or dialed dose of the primary medicament, through the single dispense interface. The reservoir preferably contains a flow distributor to ensure that substantially all the single dose of secondary medicament is forced out of the capsule by the primary medicament during an injection. The flow distributor can be a separate stand-alone insert or pin. Alternatively the flow distributor and the capsule together can be manufactured or assembled as a one-piece component where the flow distributor is integral with the reservoir or capsule. Such a unitary construction can be achieved utilizing, for example, design principles such as form fit, force fit or material fit, such as welding, gluing, or the like, or any combination thereof. The one-piece component may comprise one or more medicament flow channels, preferably one flow channel. The capsule and/or flow distributor can be constructed of any material that is compatible to the primary and secondary medicaments. Preferably the capsule and/or flow distributor can be made from compatible materials of construction that include, but are not limited to, COC (an amorphous polymer based on ethylene and norbonene, also referred to as cyclic olefin copolymer, ethylene copolymer, cyclic olefin polymer, or ethylene-norbornene copolymer); LCP (a liquid crystal polymer having an aramid chemical structure that includes linearly substituted aromatic rings linked by amide groups, and further can include partially crystalline aromatic polyesters based on p-hydroxybenzoic acid and related monomers and also highly aromatic polyesters); PBT (polybutylene terephthalate thermoplastic crystalline polymer or polyester); COP (a cyclic olefin polymer based on ring-opening polymerization of norbornene or norbornene-derivatives); HDPE (high density polyethylene); and SMMA (styrene methyl methacrylate copolymer based on methyl methacrylate and styrene). A preferred material is one that is typically used to manufacture septa or pistons (bungs) found in multi-dose medicament cartridges, however, any other material that is compatible with the drug could be used, e.g., glass, plastics or specific polymers, for example, TPE (thermo plastic elastomer); LSR (liquid silicone rubber); LDPE (low density polyethylene); and/or any kind of medical grade rubber, natural or synthetic. By "substantially all" we mean that at least about 80% of the secondary medicament is expelled from the drug delivery device, preferably at least about 90% is expelled. In the third state, preferably the module is locked so as to prevent a second delivery or insertion by means of a locking mechanism.

The combination of compounds as discrete units or as a mixed unit is delivered to the body via an integral needle. This would provide a combination drug injection system that, from a user's perspective, would be achieved in a manner that very closely matches the currently available injection devices that use standard needles.

The medicated module of the present disclosure may be designed for use with any drug delivery device with an appropriate compatible interface. However, it may be preferable to design the module in such a way as to limit its use to one exclusive primary drug delivery device (or family of devices) through employment of dedicated/coded/exclusive features to prevent attachment of a non-appropriate medicated module to a non-matching device. In some situations it may be beneficial to ensure that the medicated module is exclusive to one drug delivery device while also permitting the attachment of a standard drug dispense interface to the device. This would allow the user to deliver a combined therapy when the module is attached, but would also allow delivery of the primary compound independently through a standard drug dispense interface in situations, such as, but not limited to, dose splitting or top-up of the primary compound.

A particular benefit is that the medicated module makes it possible to tailor dose regimes when required, especially where a titration period is necessary for a particular drug. The medicated module could be supplied in a number of titration levels with obvious differentiation features such as, but not limited to, aesthetic design of features or graphics, numbering etc, so that a patient could be instructed to use the supplied medicated module in a specific order to facilitate titration. Alternatively, the prescribing physician may provide the patient with a number of "level one" titration medicated modules and then when these were finished, the physician could then prescribe the next level. A key advantage of this titration program is that the primary device remains constant throughout.

In a preferred embodiment, the primary drug delivery device is used more than once and therefore is multi-use; however, the drug delivery device may also be a single use disposable device. Such a device may or may not have a replaceable reservoir of the primary drug compound, but the present disclosure is equally applicable to both scenarios. It is also possible to have a suite of different medicated modules for various conditions that could be prescribed as one-off extra medication to patients already using a standard drug delivery device. Should the patient attempt to reuse a previously used medicated module, the present disclosure includes the locking needle guard that is activated after a first predefined travel/retraction of the needle guard/insertion of the needle. The locked needle guard would alert the patient to this situation and the inability to use the module for a second time. Visual warnings (e.g. change in color and/or warning text/indicia within an indication window on the module once insertion and/or fluid flow has occurred) can also be used. Additionally, tactile feedback (presence or absence of tactile features on the outer surface of the module hub following use) could be used as well.

A further feature is that both medicaments are delivered via one injection needle and in one injection step. This offers a convenient benefit to the user in terms of reduced user steps compared to administering two separate injections. This convenience benefit may also result in improved compliance with the prescribed therapy, particularly for users who find injections unpleasant or who have computational or dexterity difficulties.

One aspect relates to a drug delivery system. The drug delivery system may be configured to deliver two or more medicaments. The drug delivery system may be operable through a single dispense interface, e.g. a needle cannula. The drug delivery system may comprise a primary reservoir of medicament. The primary reservoir may contain at least one primary medicament, in particular a plurality of doses of the primary medicament. The drug delivery system may comprise a single dispense interface. The dispense interface may be configured for fluid communication with the primary reservoir. The drug delivery system may comprise the previously described medicated module. The single dispense interface may be part of the medicated module.

According to an embodiment, the primary medicament is configured to flow via the bypass channel and through the single dispense interface when the needle guard is in the pre-use position. Mechanical cooperation of the needle guard with rotating housings may be configured to enable the medicament in the reservoir to be dispensed along with the primary medicament through the single dispense interface.

According to an embodiment, the drug delivery system comprises a dose button. The dose button may be permanently or releasably operably connected to the primary reservoir of medicament. Activation of the dose button may cause the primary medicament to be dispensed through the single dispense interface.

The present disclosure also covers a method of delivering two medicaments stored in separate primary packages. The medicaments may both be liquid, or alternatively one or more of the medicaments may be a powder, suspension or slurry. In one embodiment the medicated module could be filled with a powdered medicament that is either dissolved or entrained in the primary medicament as it is injected through the medicated module.

These as well as other advantages of various aspects of the present invention will become apparent to those of ordinary skill in the art by reading the following detailed description, with appropriate reference to the accompanying drawings.

BRIEF DESCRIPTION OF THE DRAWINGS

Exemplary embodiments are described herein with reference to the drawings, in which.

DETAILED DESCRIPTION

Figure 1:
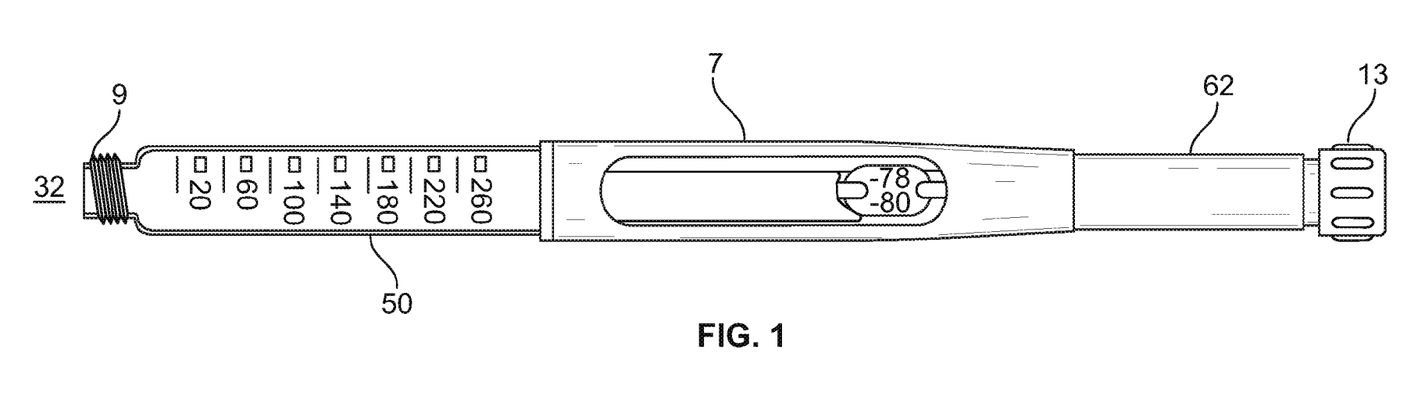
FIG. 1 illustrates one possible drug delivery device that can be used with the present invention.

The present invention administers a fixed predetermined dose of a secondary drug compound (medicament) and a variable dose of a primary or first drug compound through a single output or drug dispense interface. Setting the dose of the primary medicament by the user automatically determines the fixed dose of the secondary medicament, which preferably is a single dose contained in a capsule or reservoir having an integral flow distributor. In a preferred embodiment the drug dispense interface is a needle cannula (hollow needle). FIG. 1 illustrates one example of a drug delivery device 7 that the medicated module 4 (see FIG. 2, 3, 7, or 9) can be attached to a connection means 9 provided on cartridge holder 50 of distal end 32 of the device 7. Each medicated module 4 is preferably self-contained and provided as a sealed and sterile disposable module that has an attachment means 8 compatible to the attachment means 9 at the distal end 32 of device 7. Although not shown, the medicated module could be supplied by a manufacturer in a protective and sterile container, where the user would peel or rip open a seal or the container itself to gain access to the sterile medicated module. In some instances it might be desirable to provide two or more seals for each end of the medicated module.

Figure 2:
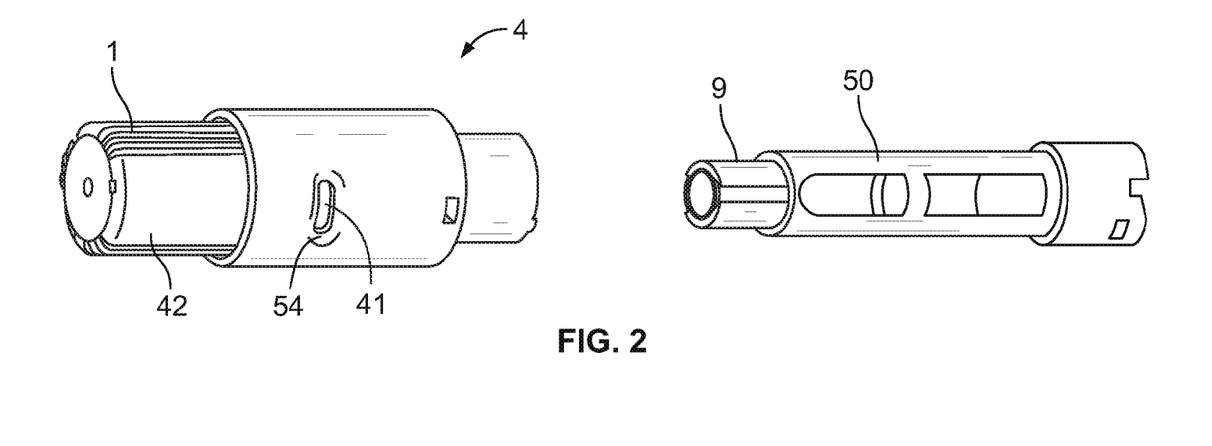
FIG. 2 illustrates an embodiment of the medicated module of the present invention, where the medicated module is separated from an attachable cartridge holder of drug delivery device.

Any known attachment means 8 can be used to attach the medicated module to the chosen drug delivery device, including all types of permanent and removable connection means, such as threads, snap locks, snap fits, luer locks, bayonet, snap rings, keyed slots, and combinations of such connections. FIGS. 1 and 2 illustrate the attachment means 9 as threaded connection and also as a unique push/pull type connection that is keyed specifically to a corresponding push/pull type connection on medicated module 4, respectively. FIG. 4 shows the medicated module with a corresponding screw thread 8 associated with hub 51. The embodiments shown in FIGS. 3-10 have the benefit of the secondary medicament as a single dose being contained entirely within a capsule 31, and specifically in a reservoir 22, hence minimizing the risk of material incompatibility between the secondary medicament and the materials used in the construction of the medicated module 4, specifically housing 10, rotating housing 52, or any of the other parts used in the construction of the medicated module.

Figure 11:
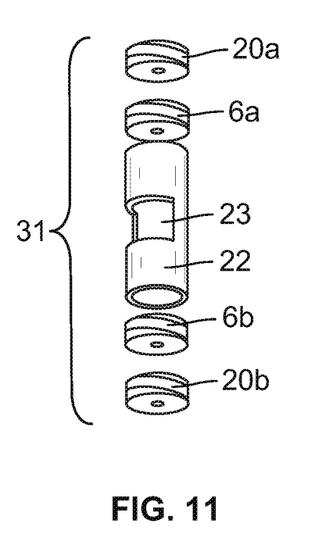
FIG. 11 is an exploded view of the capsule containing the secondary medicament of the embodiments shown in FIGS. 3-10.
Figure 12:
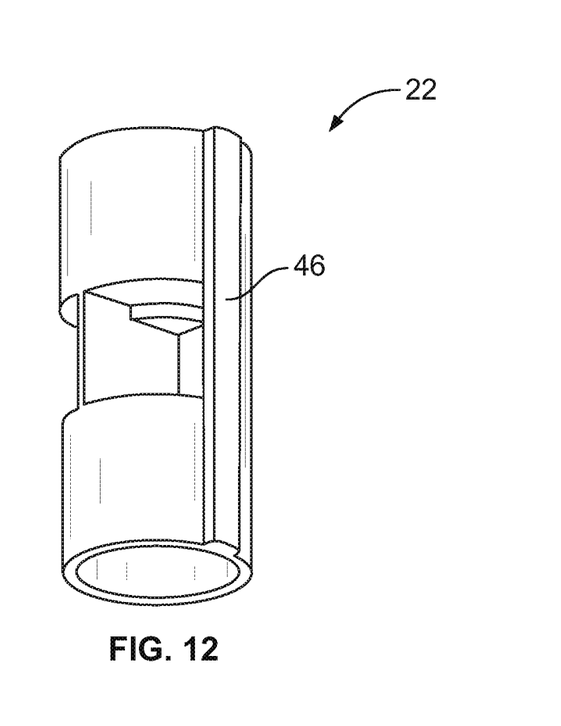
FIG. 12 is a perspective view of the capsule showing part of the bypass of the embodiments shown in FIGS. 3-10.
Figure 13:
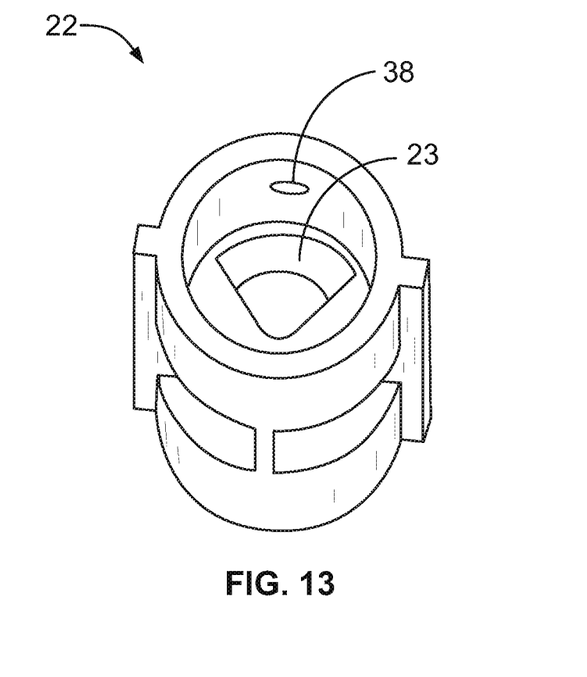
FIG. 13 is another perspective view of the capsule showing the flow distributor.

To minimize the residual volume of the secondary medicament, caused by recirculation and/or stagnant zones, that might remain in capsule 31 at the end of the dispense operation, it is preferable to have a flow distributor 23 as an integral part of reservoir 22 (see FIGS. 11 and 13). The reservoir 22 containing the single dose of the secondary medicament can be sealed with septa 6a and 6b, which are fixed to the capsule using keepers or plugs 20a and 20b. Preferably the keepers have fluid channels that are in fluid communication with needles 3 and 5 and with bypass 46, which is preferably part of the inside surface of bypass housing 52. Together this fluid path allows priming of the drug delivery device before injection. Preferably the reservoir, flow distributor, keepers, and bypass can be made from materials that are compatible with the primary medicament. Examples of compatible materials of construction include, but are not limited to, COC (an amorphous polymer based on ethylene and norbonene, also referred to as cyclic olefin copolymer, ethylene copolymer, cyclic olefin polymer, or ethylene-norbornene copolymer); LCP (a liquid crystal polymer having an aramid chemical structure that includes linearly substituted aromatic rings linked by amide groups, and further can include partially crystalline aromatic polyesters based on p-hydroxybenzoic acid and related monomers and also highly aromatic polyesters); PBT (polybutylene terephthalate thermoplastic crystalline polymer or polyester); COP (a cyclic olefin polymer based on ring-opening polymerization of norbornene or norbornene-derivatives); HDPE (high density polyethylene); and SMMA (styrene methyl methacrylate copolymer based on methyl methacrylate and styrene). The needle pierceable septa, bungs, and/or seals that are used with both the capsule and the primary medicament cartridge can be manufactured using TPE (thermo plastic elastomer); LSR (liquid silicone rubber); LDPE (low density polyethylene); and/or any kind of medical grade rubber, natural or synthetic.

The design of flow distributor 23 may help to expel at least about 80% of the secondary medicament from reservoir 22 through the distal end of needle 3. Most preferably at least about 90% should be expelled. Ideally, displacement of the primary medicament in a primary reservoir (not shown) contained in cartridge holder 50 and through the capsule 31 will displace the single dose of the secondary medicament stored in reservoir 22 without substantial mixing of the two medicaments.

Attachment of the medicated module 4 to the multi-use device 7 causes proximal needle 5 to penetrate a septum (not shown) sealing the distal end of the cartridge of primary medicament positioned in cartridge holder 50 of the multi-use device 7. Once needle 5 has passed through the septum of the cartridge, fluid connection is made between the primary medicament and the needle 5. At this point, the system can be primed by dialing out a small number of units (or cocking the device if only a single dose selection is possible) using dose dial sleeve 62. One the device 7 is primed, then activation of the needle guard 42 allows dispense of the medicaments by subcutaneously injecting the medicaments via activation of a dose button 13 on device 7. The dose button of the present disclosure can be any triggering mechanism that causes the dose of the primary medicament that was set by the dose dial sleeve 62 to move towards the distal end 32 of the device. In a preferred embodiment the dose button is operably connected to a spindle that engages a piston in the primary reservoir of the primary medicament. In a further embodiment the spindle is a rotatable piston rod comprising two distinct threads.

In each embodiment the medicated module 4 contains a capsule 31 comprising a reservoir 22, two keepers 20*a* and 20*b*, and two seals 6*a* and 6*b*. Reservoir 22 contains a fixed single dose of a secondary medicament. In some cases this secondary medicament may be a mixture of two or more drug agents that can be the same or different from the primary drug compound in the drug delivery device 7. Preferably the capsule is permanently fixed within the medicated module, however, in some cases it may be preferred to design the module such that the capsule can be removed when empty and replaced with a new capsule. Capsule 31 has ends that are sealed with pierceable membranes or septa 6*a* and 6*b* that provide a hermetically sealed and sterile reservoir 22 for the secondary medicament.

A primary or proximal or upper engagement needle 5 can be fixed in hub 51 as in embodiments of FIGS. 7-10 or connected to a moving upper hub 14 connected to the proximal end of housing 10 of the module and configured to engage capsule 31 when needle guard is moving in the proximal direction during injection. The outlet, distal, or lower needle 3, is preferably mounted in lower hub 15 and initially protrudes into lower keeper 20*b* (not shown for clarity reasons). The proximal end of needle 3 pierces the lower septum 6*b* when the lower hub is moved axially as the needle guard 42 is retracted into outer housing 10 during injection.

When first attached to the delivery device, the medicated module 4 is set at a pre-use or starting position. Preferably, an indicator 41 shows through window 54 to inform the user of the pre-use condition of the medicated module. The indicator is preferably a color stripe or band (not shown) on the outer surface of the proximal end of needle guard 42 visible through an aperture 54 in the outer body. The needle guard 42 is slidably engaged with inner surface of outer housing 10 by engagement of rib 2 and channel 1 on the inside surface the outer housing. Of course, the rib and channel can be reversed as shown in FIG. 2 where channel 1 is located on the outside surface of needle guard 42. Preferably, retention snaps (not shown) prevent the needle guard from disengaging the outer housing at its fully extended position. Connected to the outer housing 10 is bypass housing 52, which contains capsule 31. A portion of the proximal end of housing 10 defines an upper hub 51 that is configured to connect to an appropriate primary drug delivery like the type shown in FIG. 1. Optionally, as illustrated in FIG. 4, a shoulder cap 25 may be added to the proximal outer surface of outer housing 10. This shoulder cap can be configured to serve as indicia to identify to a user the type/strength of medicament contained in the module. The indicia can be tactile, textual, color, taste or smell.

Figure 3:
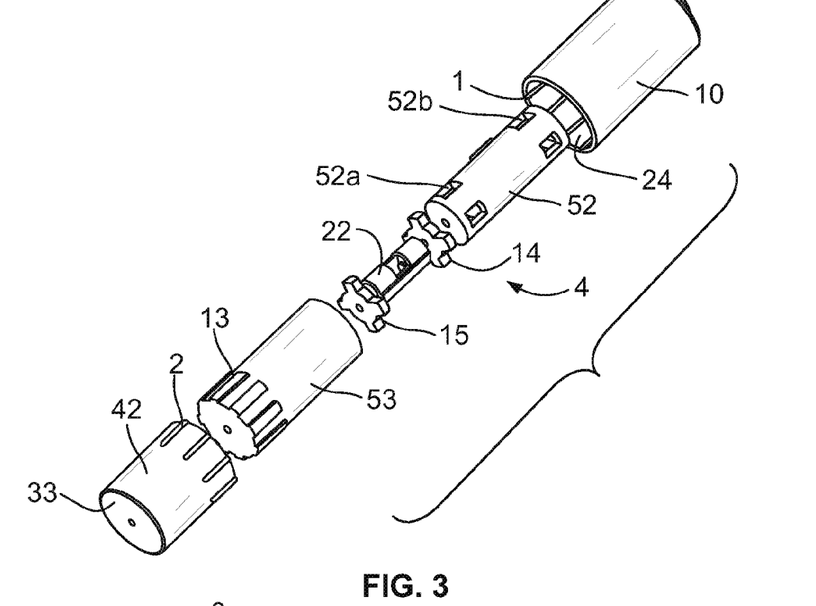
FIG. 3 illustrates an exploded perspective view of one possible embodiment of the medicated module of the present disclosure.
Figure 4:
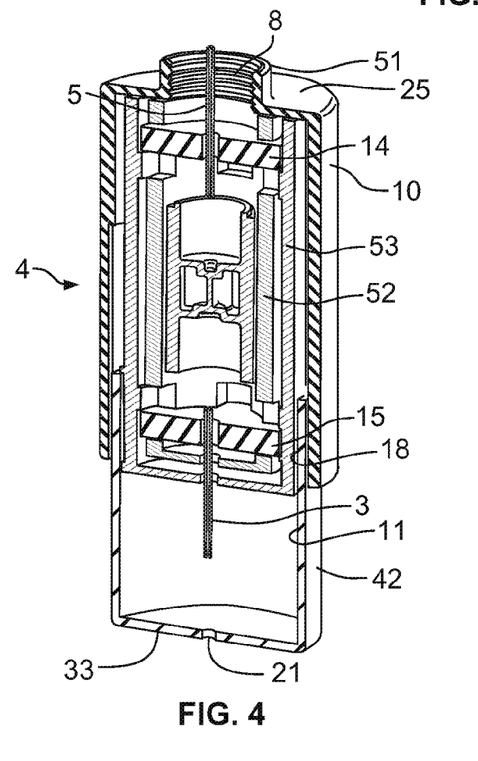
FIG. 4 illustrates a first sectional view of select components of the medicated module illustrated in FIG. 3.
Figure 5:
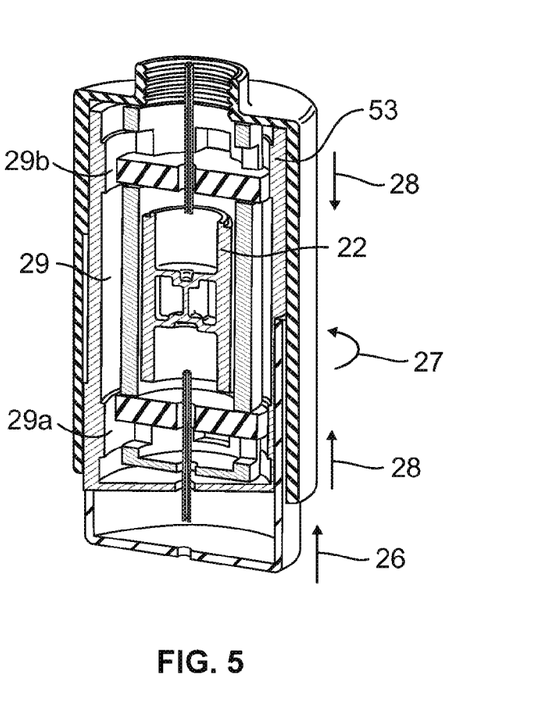
FIG. 5 illustrates a second sectional view of select components of the medicated module illustrated in FIG. 3 as the needle guard is retracted.
Figure 6:
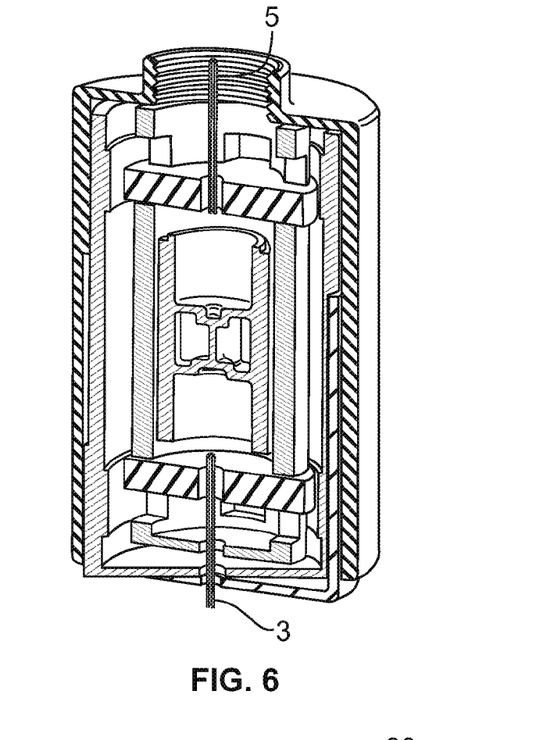
FIG. 6 illustrates a third sectional view of select components of the medicated module illustrated in FIG. 3 when the needle guard is fully retracted.

FIGS. 3-6 shows a first embodiment of medicated module 4. Specifically, FIG. 3 shows an exploded perspective view of the main components of the module, but for clarity reasons, such items as the needles, biasing member, etc. are not shown. The inner wall 11 of the needle guard has threads 18 that are in threaded engagement with the external surface 13 of rotating housing 53. When the needle guard is retracted (i.e., moved in the proximal direction, such as during an injection) the needle guard is prevented from rotating by engagement of rib 2 with channels or splines 1 on the inner surface 24 of the outer housing 10. Since the needle guard cannot rotate as it moves axially and the rotating housing cannot move axially, the rotating housing must rotate about the threads 13 and 18. FIG. 5 illustrates this motion with needle guard directional arrow 26 and rotating housing directional arrow 27. The internal surface 29 of the rotating housing 53 has threads 29*a* and 29*b* that are in threaded engagement with the lower and upper hubs, 15 and 14, respectively. The upper and lower hubs engage the threaded internal surface 29 because a portion of each hub extends through cutouts 52*a* and 52*b* of bypass housing 52, which prevents both hubs from rotating. Rotation of the rotating housing causes the upper hub to move distally and the lower hub to move proximally (see directional arrows 28) whereby the upper needle 5 and the lower needle 6 come into fluid communication with the medicament in reservoir 22. FIG. 6 shows the needle guard fully refracted, the reservoir engaged with the needles, and the rotating housing fully rotated.

Figure 7:
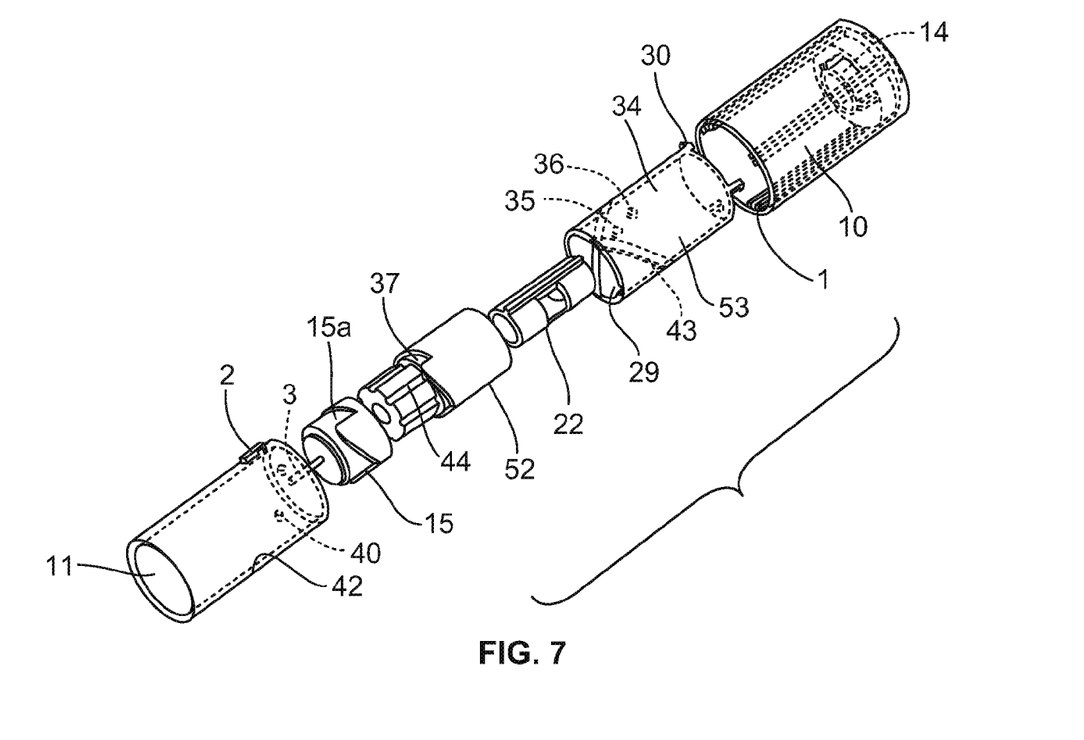
FIG. 7 illustrates an exploded perspective view of a second possible embodiment of the medicated module of the present disclosure.
Figures 8, 9:
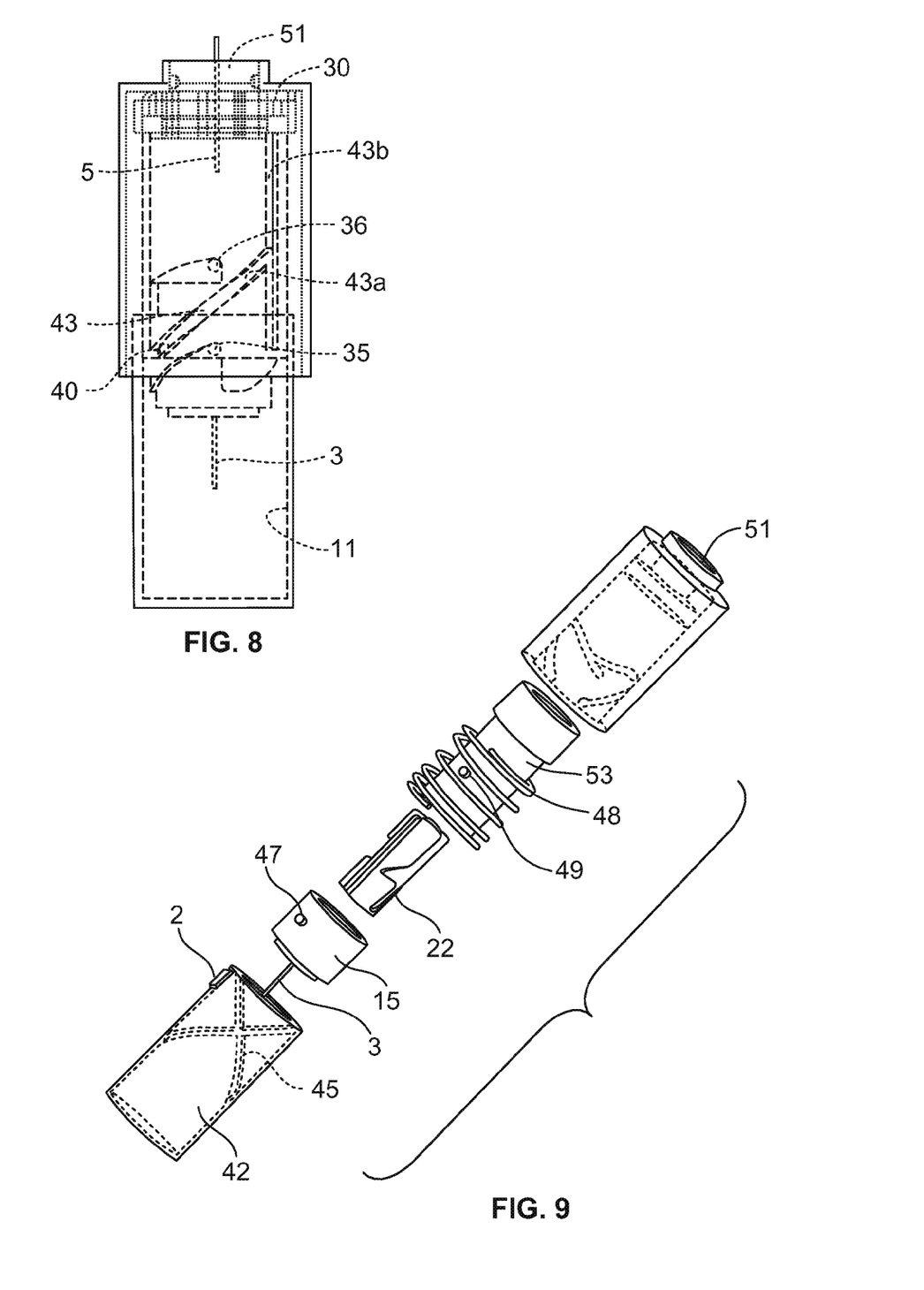
FIG. 8 illustrates a transparent perspective view of the embodiment of FIG. 7.
FIG. 9 illustrates an exploded perspective view of a third possible embodiment of the medicated module of the present disclosure.
Figure 9A:
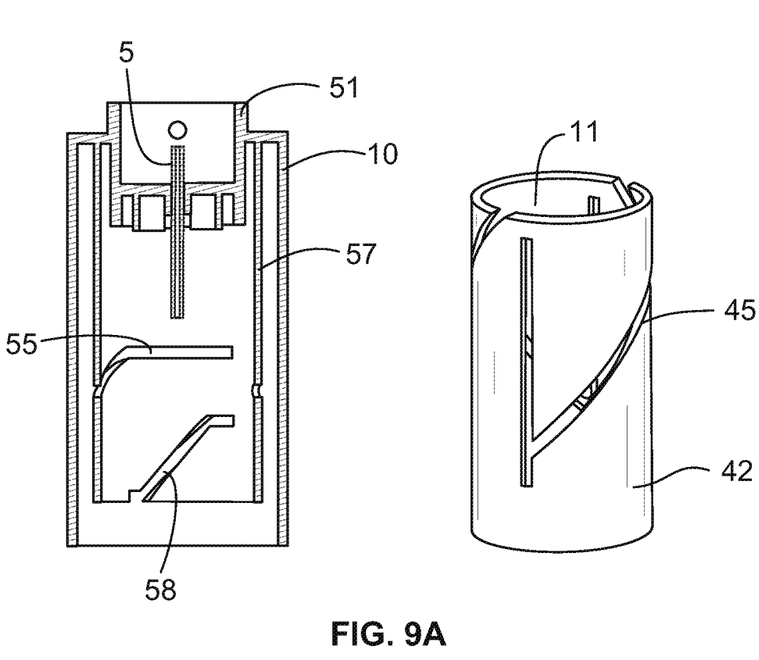
FIG. 9a illustrates cross-sectional views of the outer and inner housing and the needle guard.

Another embodiment of the medicated module is illustrated in FIGS. 7-8, where the inner wall 11 of the needle guard 42 has a drive tooth 40 that engages a non-linear track 43 on an outside surface 34 of the rotating housing 53. Track 43 has a helical portion 43*a* and a linear portion 43*b*. Rotating housing 53 is fixed axially to the inner proximal end of outer housing 10 through connectors 30, which allow the rotating housing to freely rotate relative to needle guard 42 and outer housing 10. An internal surface 29 of the rotating housing 53 has one or more radial protrusions 35 that engage the lower hub 15 in helical path 15*a* causing it to move proximally when the needle guard 42 is retracted into the outer housing 10. The lower hub 15 has internal splines (not shown) that engage cooperating splines 44 on the distal outer surface of bypass housing 52. The proximal internal surface of the bypass housing is splined to the outer housing to prevent rotation of the bypass housing, but allow axial movement. The proximal end of the bypass housing 52 comprises ribs or protrusions on the inner surface (not shown) configured to engage with splines on the outside of upper hub 14, which, in this embodiment, is fixed to the outer housing 10 at the proximal end as shown in FIG. 7. Alternatively, hub 14 could be an integral part of the outer housing 10. Alternatively, hub 51 could comprise upper hub 14 holding the upper needle 5. However, the bypass housing 52 is splined at its proximal end to the outer housing 10 allowing axial movement but preventing rotation of the bypass housing 52 relative to the outer housing 10. The splined connection between the lower hub 15 and bypass housing 52 prevents the lower hub from rotating, but allows the lower hub to move axially. A second radial protrusion 36 on the internal surface 29 of the rotating housing 53 engages the outside surface of the of the bypass housing in path 37 to cause the bypass housing to move proximally when the needle guard retracts.

As the needle guard retracts axially (not rotationally), the needle guard drive toot or pin 40 engaged in the helical path 43*a* causes the rotating housing to rotate (but not move axially). The rotation of the rotating housing causes pins 35 and 36 to rotate along paths 15*a* and 37, respectively. Since lower hub 15 and bypass housing 52 cannot rotate, both structures are forced to move proximally causing needle 3 to engage the distal end of reservoir 22. Reservoir 22 moves proximally with the lower hub and by pass housing as the rotating housing rotates and eventually is moved to engage the distal end of needle 5 in hub 51. Preferably, the lower hub and the bypass housing move together so that both needles engage the reservoir simultaneously. Once the pip 40 enters the linear portion 43b of track 43, rotation of the rotating housing stops and there is no further movement of the lower hub, bypass housing or reservoir. The needle guard continues to move linearly until it reaches the end of its stroke. The configuration of paths 15a and 37 can be adjusted to provide the optimal movement of the lower hub and bypass housing.

Figure 10:
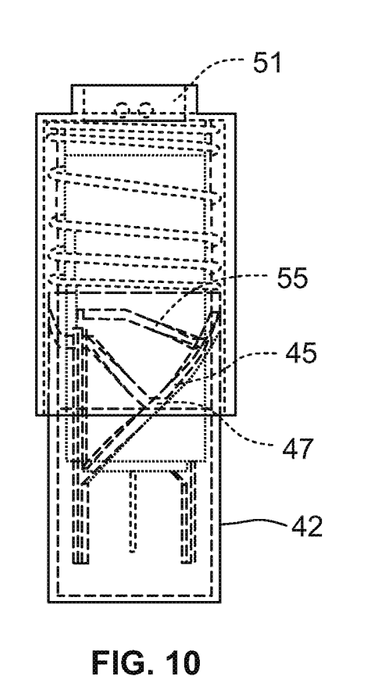
FIG. 10 illustrates a transparent perspective view of the embodiment of FIG. 9.

FIGS. 9 and 10 illustrate another embodiment of the medicated module where the inner wall 11 of the needle guard 42 has a non-linear track 45 that engages one or more radial protrusions 47 on an outside surface of the lower hub 15 such that proximal axial movement of the needle guard causes the lower hub to rotate and move proximally to cause the lower needle 3 to engage the reservoir 22. In this particular embodiment, the rotating housing 53 is the same structure as the bypass housing and also has one or more radial protrusions 49 on the external surface that engages the needle guard track 45. An inner housing 57 is connected to the outer housing 10 and has non-linear tracks 55 and 58 engaged with the radial protrusions 49 and 47, respectively, on the lower hub and on the rotating housing. The non-linear tracks 55 and 58 of the inner housing cause the lower hub and rotating housing to move axially as they are rotated due to the linear movement of needle guard 42.

Pins 47 and 49 travel in track 45 of the needle guard 42. Since rib 2 of the needle guard is splined to inner wall 11 on the outer housing (not shown), rotation is prevented but axial movement is allowed, which causes rotation of lower hub 15 and rotating housing 53. The pins 47 and 49 also travel in slots 55 and 58 in the inner body 57. Rotation of the lower hub and rotating housing relative to the slots in inner housing 57 causes them to move axially in the proximal direction. The slot geometry can be adjusted to give desired and required movement for each component.

In each of the embodiments described, the starting point of the medicated module has the reservoir 22 in neutral or suspended state, where primary medicament from the cartridge in cartridge holder 50 of device 7 can flow through needle 5 into keeper 20a, through by pass hole 38 (see FIG. 13) into bypass 46 and into keeper 20b, and eventually out through needle 3. This flow configuration allows a user to perform a priming step or procedure by setting a small dose of the primary medicament using the dose dial sleeve 62 and dose button 13 on the drug delivery device 7.

A biasing member, such as compression spring 48 (see FIGS. 9-10) can be used in each of the above described embodiments and is positioned between the proximal end of the outer housing 10 and the inner proximal face of needle guard 42 to bias the needle guard 42 into an extended (guarded) position as illustrated in FIGS. 4, 8 and 10.

One possible feature of our medicated module assembly is the inclusion of user feedback that is given when the assembly is used. In particular, the assembly could emit an audible and/or tactile "click" to indicate to the user that they have firstly triggered the device and secondly reached a "commit" point such that the needle guard will lock safely out upon completion of the injection/removal of the needle guard from the injection site.

As mentioned, the distal end of the guard 42 has a planar surface 33 that provides an added measure of safety and reduces the pressure exerted by the needle guard on the injection site during an injection with our needle assembly. Because the planar surface 33 substantially covers access to needle 3 a user is prevented from gaining access to the distal tip of the needle after the assembly is in the locked position. Preferably, the diameter D of needle pass through hole 21 in the planar surface is no more than 10 times that of the outer diameter of needle cannula 3.

The outer proximal surface of the needle guard 42 preferably has indicia (not shown) that are preferably at least two different color stripes or bands, each of which is sequentially visible through the opening or window 54 in outer housing 10. One color could designate the pre-use or prime state of the module and the other color would indicate that the module is in finished or locked state, another color could be used to denote the transition through the trigger or "commit" point in case a user stops injection after trigger point but before "commit" point. For example, a green color could be the pre-use position and a band of red color could be used to indicate that the module has been used and is locked and an orange color could indicate that the device has been triggered but not locked out. Alternatively, graphics, symbols or text could be used in place of color to provide this visual information/feedback. Alternatively these colors could be displayed using the rotation of the bypass cavity and printed on or embedded into the bypass housing. They could be visible through the aperture by ensuring that the needle guard is made form a transparent material.

In any of the above described embodiments of the present disclosure the secondary medicament may be either in a powdered solid state, any fluid state contained within the secondary reservoir or capsule, or coated to the inside surface of the drug dispense interface. The greater concentration of the solid form of the medicament has the benefit of occupying a smaller volume than the liquid having lower concentration. This in turn reduces the ullage of the medicated module. An additional benefit is that the solid form of the secondary medicament is potentially more straightforward to seal in the secondary reservoir than a liquid form of the medicament. The device would be used in the same manner as the preferred embodiment with the secondary medicament being dissolved by the primary medicament during dispense.

To minimize diffusion of the secondary medicament contained in the capsule within the medicated module into the primary medicament during dispense of the medicaments the reservoir 22 has an integral flow distributor 23. This flow distributor also ensures efficient expulsion of the secondary medicament from the system and greatly minimizes residual volume. One possible embodiment of the reservoir 22 and flow distributor 23 is illustrated in FIG. 13. Preferably the reservoir and flow distributor are manufactured as a single part from materials that are compatible with the secondary medicament, most preferably as a single molded piece. A preferred material would be that typically used to manufacture septa or pistons (bungs) found in multi-dose medicament cartridges, although any material that is compatible with the medicament during long term storage would be equally applicable. The flow distributor 23 is configured and positioned in reservoir 22 such that the secondary medicament fills flow channels that are defined by the shape and location of one or more channels (not shown) inside the reservoir. The shape of the flow channels can be optimized for a plug flow of medicament by varying the dimensions of the flow distributor and/or channels.

The cross-sectional area of the annulus formed between the flow distributor and the wall of the reservoir should be kept relatively small. The volume available to store the secondary medicament would equal the internal volume of the reservoir minus the volume of the flow distributor. Therefore if the volume of the flow distributor is marginally smaller than the internal volume of the capsule, a small volume is left which the secondary medicament occupies. Hence the scale of both the capsule and the flow distributor can be large while storing a small volume of medicament. Resultantly for small volumes of secondary medicament (e.g. 50 micro liters) the reservoir can be of an acceptable size for handling, transport, manufacture, filling and assembly.

Preferably the medicated module is provided by a drug manufacturer as a stand-alone and separate device that is sealed to preserve sterility. The sterile seal of the module is preferably designed to be opened automatically, e.g. by cutting, tearing or peeling, when the medicated module is advanced or attached to the drug delivery device by the user. Features such as angled surfaces on the end of the injection device or features inside the module may assist this opening of the seal.

The medicated module of the present disclosure should be designed to operate in conjunction with a multiple use injection device, preferably a pen-type multi-dose injection device, similar to what is illustrated in FIG. 1. The injection device could be a reusable or disposable device. By disposable device it is meant an injection device that is obtained from the manufacturer preloaded with medicament and cannot be reloaded with new medicament after the initial medicament is exhausted. The device may be a fixed dose or a settable dose and preferably a multi-dose device, however, in some cases it may be beneficial to use a single dose, disposable device.

A typical injection device contains a cartridge or other reservoir of primary medication. This cartridge is typically cylindrical in shape and is usually manufactured in glass. The cartridge is sealed at one end with a rubber bung and at the other end by a rubber septum. The injection device is designed to deliver multiple injections. The delivery mechanism is typically powered by a manual action of the user, however, the injection mechanism may also be powered by other means such as a spring, compressed gas or electrical energy. In a preferred embodiment, the delivery mechanism comprises a spindle that engages a piston in the reservoir. In a further embodiment the spindle is a rotatable piston rod comprising two distinct threads.

Exemplary embodiments of the present invention have been described. Those skilled in the art will understand, however, that changes and modifications may be made to these embodiments without departing from the true scope and spirit of the present invention, which is defined by the claims.

The invention claimed is:

1. A medicated module attachable to a drug delivery device, comprising,
   a) an outer housing having an inner surface, a proximal end and a distal end, where the proximal end has an upper hub having a connector configured for attachment to a drug delivery device;
   b) a bypass housing within the outer housing;
   c) a reservoir within the bypass housing comprising a single dose of a medicament;
   d) a lower hub holding a lower needle and an upper needle hub holding an upper needle;
   e) a needle guard having an inner wall and is slidably connected to the inner surface of the outer housing to prevent rotation of the needle guard when moved axially; and
   f) a rotating housing having an internal surface and an external surface, where the external surface is engaged with the inner wall of the needle guard such that axial movement of the needle guard in the proximal direction causes,
      i. rotation of the rotating housing; and
      ii. engagement of the lower needle with the reservoir to establish fluid communication with the medicament.

2. The medicated module of claim 1 where the inner wall of the needle guard is in threaded engagement with the external surface of the rotating housing and the internal surface of the rotating housing is in threaded engagement with the lower and upper hubs such that the rotation of the rotating housing causes the upper hub to move distally and the lower hub to move proximally whereby the upper needle and the lower needle come into fluid communication with the medicament.

3. The medicated module of claim 1 where the inner wall of the needle guard has a drive tooth that engages a non-linear track on an outside surface of the rotating housing, where the internal surface of the rotating housing has a radial protrusion that engages the lower hub causing it to move proximally when the needle guard is retracted into the outer housing.

4. The medicated module of claim 3 where the lower hub is splined to a bypass housing on an outside surface and has an inside surface that is splined to the outer housing to prevent rotation of the lower hub and the bypass housing.

5. The medicated module of claim 4 where a second radial protrusion on the internal surface of the rotating housing engages the outside surface of the of the bypass housing to cause the bypass housing to move proximally when the needle guard retracts.

6. The medicated module of claim 3 where proximal movement of the lower hub causes the lower needle to come into fluid engagement with the medicament.

7. The medicated module of claim 1 where inner wall of the needle guard has a non-linear track that engages a radial protrusion on an outside surface of the lower hub such that proximal axial movement of the needle guard causes the lower hub to rotate and move proximally to cause the lower needle to engage the reservoir.

8. The medicated module of claim 7 where the rotating housing is the same structure as a bypass cavity and has a radial protrusion on the external surface that engages the non-linear track.

9. The medicated module of claim 8 further comprising an inner housing connected to the outer housing and having a first non-linear track engaged with radial protrusion on the lower hub and a second non-linear track engaged with radial protrusion on the rotating housing, where the non-linear tracks of the inner housing causes the lower hub and rotating housing to move axially as they are rotated.

10. The medicated module of claim 1 further comprising a biasing member engaged between the needle guard and the outer housing.

11. The medicated module of claim 1 where a rib on the needle guard outer wall engages a channel on the inner surface of the outer housing to prevent the needle guard from rotating during axial movement relative to the outer housing.

12. The medicated module of claim 1 where the reservoir comprises a single molded component having an internal cavity with an integral flow distributor.

13. The medicated module of claim 1 where the medicament in the reservoir comprises at least one of a GLP-1, an Insulin, and a premix of insulin and a GLP-1.

14. The medicated module of claim 1 having a first state where the needles are in fluid communication with a bypass around the reservoir and a second state where the needles are in fluid communication with a medicament in the reservoir.

15. The medicated module of claim 14 wherein the bypass around the reservoir is configured such that when the medicated module is connected to the drug delivery device containing a primary medicament and prior to piercing the seals of the reservoir, the needles are in fluid communication with the primary medicament and the bypass.

16. The medicated module of claim 1 wherein the medicament in the reservoir is sealed with septa which are fixed with keepers or plugs, wherein the keepers have fluid channels that are in fluid communication with the needles.

17. The medicated module of claim 16, wherein the bypass housing further comprises a bypass in fluid communication with the fluid channels of the keepers.

18. A drug delivery system configured to deliver two or more medicaments operable through a single dispense interface, comprising,
- a primary reservoir of medicament containing at least one drug agent;
- a dose button operably connected to the primary reservoir of medicament;
- a single dispense interface configured for fluid communication with the primary reservoir; and
- the medicated module of claim 1.

* * * * *